United States Patent

Mawhirt et al.

Patent Number: 5,772,677
Date of Patent: Jun. 30, 1998

[54] INCISION DEVICE CAPABLE OF AUTOMATIC ASSEMBLY AND A METHOD OF ASSEMBLY

[75] Inventors: James A. Mawhirt, Brooklyn, N.Y.; Anthony F. Kuklo, Jr., Bridgewater, N.J.; Christopher R. Vander Wal, Oakland, N.J.; Peter J. Sklenar, Somerville, N.J.

[73] Assignee: International Technidyne Corporation, Edison, N.J.

[21] Appl. No.: 718,774

[22] Filed: Sep. 24, 1996

[51] Int. Cl.⁶ .................................................. A61B 17/14
[52] U.S. Cl. ........................................ 606/181; 606/182
[58] Field of Search ................................... 606/181, 182, 606/180

[56] References Cited

U.S. PATENT DOCUMENTS

| | | |
|---|---|---|
| 3,760,809 | 9/1973 | Campbell, Jr. . |
| 4,539,988 | 9/1985 | Shirley et al. . |
| 4,553,541 | 11/1985 | Burns . |
| 4,643,189 | 2/1987 | Mintz . |
| 5,133,730 | 7/1992 | Biro . |
| 5,212,879 | 5/1993 | Biro . |
| 5,314,441 | 5/1994 | Cusack et al. ......................... 606/182 |
| 5,395,388 | 3/1995 | Schraga . |

Primary Examiner—Gary Jackson
Assistant Examiner—Kevin Truong
Attorney, Agent, or Firm—Plevy & Associates

[57] ABSTRACT

An apparatus for implementing a skin incision has a torsion spring and a method of assembling the apparatus. The apparatus has a housing having a pair of housing sections, each of the housing section having a base and a plurality of walls. The housing defines an inner space and an exterior. A pivot arm is pivotally mounted to a base of a housing section. The pivot arm is guided between a first position and a second position by a follower in a cam carried by the housing. A torsion spring carried by a spring post is coupled to the arm to exert a spring force on the arm in the first position. The housing has an indentation with a raised level and a lower groove on the base for receiving a portion of the spring post. The opening through the base extends from the lower groove. The spring post has a cylindrical base portion adapted to be received by the indentation in the base and a detent portion. The detent portion has a circular segment detent portion and a turn element accessible from the exterior of the housing. The circular segment detent portion is adapted to engage the raised level of the indentation in the install position and be retained in the lower groove in the loaded position. A trigger mechanism is received in the housing and acts with the pivot arm when activated whereby the arm moves from the first position to the second position due to the spring energy.

8 Claims, 8 Drawing Sheets

INCISION DEVICE CAPABLE OF AUTOMATIC ASSEMBLY AND A METHOD OF ASSEMBLY

FIELD OF THE INVENTION

The invention relates to an apparatus for providing a skin incision in order to cause bleeding and more particularly to a disposable device which provides a precisely controlled incision in the skin of the patient, can be automatically assembly, and can have its spring wound during final assembly.

BACKGROUND OF THE INVENTION

Disposable skin incision devices have been produced and marketed for many years. In a majority of these skin incision devices, a trigger is pushed which causes a blade to project out of a slot in the housing and then to retract back into the housing. The skin incision device has a spring or a flexural member which upon triggering produces the force to project the blade out of the housing into the skin and retract the blade. A skin incision device having a spring is described in U.S. Pat. No. 4,643,189 entitled "Apparatus for Implementing A Standardized Skin Incision" which issued to Mintz on Feb. 17, 1987, and is incorporated herein by reference.

In skin incision devices which use a spring, the spring must be tensioned or cocked in order to achieve the desired result. In assembling the skin incision device, the spring must be tensioned and then held in tension while the skin incision device is being assembled.

It would be desirable to assemble the spring in the skin incision device in a non-tension position and then tension the spring at a later time.

SUMMARY OF THE INVENTION

This present invention is directed to an apparatus for implementing a skin incision and a method of assembling the apparatus. The apparatus has a housing having a pair of housing sections. Each of the housing sections has a base and a plurality of walls. The housing defines an inner space and an exterior. A pivot arm is pivotally mounted to a base of a housing section. The pivot arm is guided between a first position and a second position by a follower in a cam carried by the housing. A torsion spring carried by a spring post is coupled to the arm to exert a spring force on the arm in the first position. The housing has an indentation with a raised level and a lower groove on the base for receiving a portion of the spring post. The opening through the base extends from the lower groove. The spring post has a cylindrical base portion adapted to be received by the indentation in the base and a detent portion. The detent portion has a circular segment detent portion and a turn element accessible from the exterior of the housing. The circular segment detent portion is adapted to engage the raised level of the indentation in the install position and be retained in the lower groove in the loaded position. A trigger mechanism is received in the housing and acts with the pivot arm when activated whereby the arm moves from the first position to the second position due to the spring energy.

One object, feature, and advantage resides in the housing having an indentation with a raised level and a lower groove on the base for receiving a portion of the spring post, and the circular segment detent portion of the spring post adapted to engage the raised level of the indentation in the install position and be retained in the lower groove in the loaded position. Another object, feature, and advantage resides in the torsion spring having a circular core and a pair of legs, the circular core of the torsion spring encircling the spring post, and the spring post having a slot for receiving one of the legs of the spring.

Further objects, features, and advantages of the present invention will become more apparent to those skilled in the art as the nature of the invention is better understood from the accompanying drawings and detailed descriptions.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

FIG. 4 is an inside view of a second housing section of the apparatus;

DETAILED DESCRIPTION OF THE PREFERRED EMBODIMENT

Figure 1A:
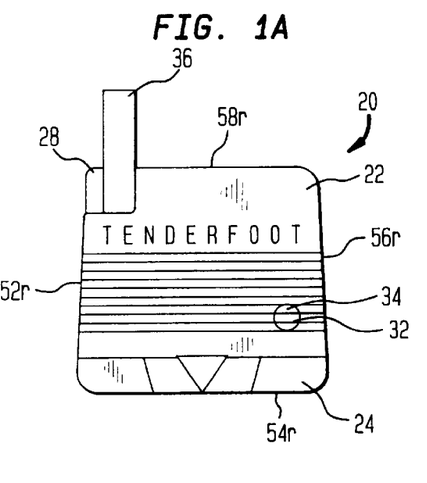
FIG. 1A is a front view of the skin incision apparatus. Selected parts are shown in hidden line.
Figure 1B:
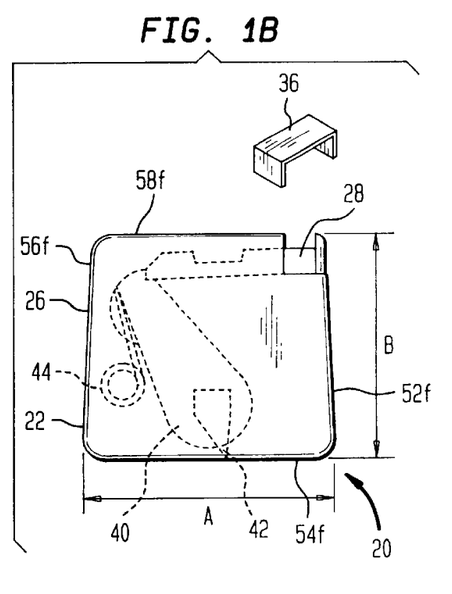
FIG. 1 is a rear view of a skin incision apparatus, according to the invention

Referring now to the drawings, wherein like numerals indicate like elements, there is illustrated in FIG. 1 a rear view of an apparatus for skin incision which has been identified by the numeral 20.

The skin incision apparatus 20 has a housing 22 having a pair of housing sections 24 and 26, only one section, the rear section 24, seen in FIG. 1. A trigger mechanism 28 of and for activating the skin incision apparatus 20 projects through an opening 30, as best seen in FIGS. 3 and 4, formed between the two sections 24 and 26 of the housing 22. The trigger mechanism 28 is also referred to as a plunger. The rear section 24 of the housing 22 has a hole 32 through which a portion of a spring post 34 projects.

The skin incision apparatus 20 has a keeper or safety device 38 which can be removed from a safety position surrounding a portion of the trigger mechanism 28 to prevent inadvertent operation. The keeper 38 is shown removed in FIG. 1A.

The front housing section 26 with the surface configuration not shown and selected components of the skin incision apparatus 20 are shown in hidden line is seen in FIG. 1A. The skin incision apparatus 20 has, in addition to the housing 22, the trigger mechanism 28, and the spring post 34, not seen in FIG. 1A, a pivot arm 40 which carries a blade 42 , and a torsion spring 44. The pivot arm 40, the spring post 34, and the torsion spring 44 are located in an inner space 46 defined by the housing sections 24 and 26. When the trigger mechanism 28 is pushed/pressed inwardly, to the left in FIG. 1A, the trigger mechanism 28 releases the pivot arm 40 and the torsion spring 44 rotates the pivot arm 40 such that the blade 42 passes through a slot 48, as seen FIG. 2, and retracts back into the housing 22.

Figure 2:
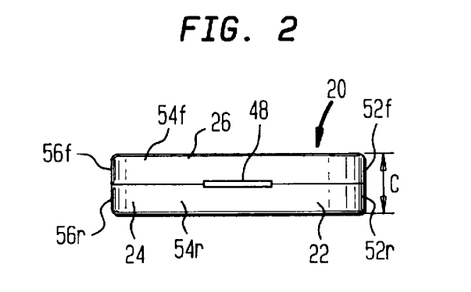
FIG. 2 is a bottom plan view of the apparatus.

In order to gain some insight into the dimensions of an actual unit, a typical unit has a height A of approximately 1.19 inches with a bottom length B of 1.125 inches; the top length being slightly less than the bottom length. The unit has width C, as seen in FIG. 2, of about 0.4375 inches.

Each of the housing sections 24 and 26 has a base 50 and four walls 52, 54, 56, and 58 projecting from the base 50. The bottom wall 54 of each of the housing sections 24 and 26 is shown in FIG. 2. The bottom walls 54*f* and 54*r* are joined together to define the slot 48, through which the blade 42 passes during operation or when activated.

The base 50*r* and the four walls 52*r*, 54*r*, 56*r*, and 58*r* projecting from the base 50*r* of the rear housing section 24 are seen in FIG. 3. The four walls 52*r*, 54*r*, 56*r*, and 58*r* and base 50*r* define a portion of the inner space 46. Located generally where two walls join to form a corner is an opening 60.

Figure 3A:
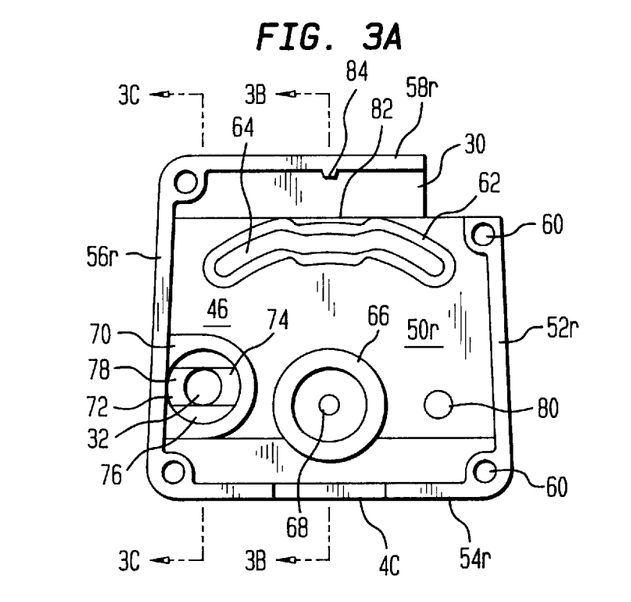
FIG. 3A is a sectional view taken along the line 3A—3A in FIG. 3.
Figure 3B:
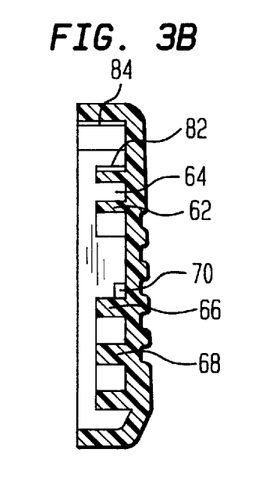
FIG. 3B is a sectional view taken along the line 3B—3B in FIG. 3.
Figure 3C:
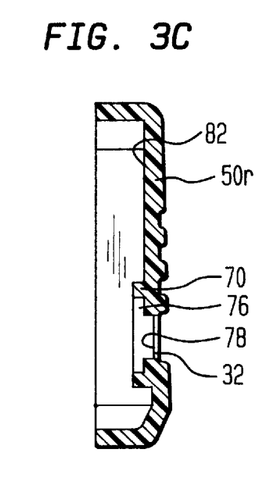
FIG. 3 is an inside view of a first housing section of the apparatus.

Referring to FIGS. 3 and 3A, the rear housing section 24 has a raised portion or bulkhead 62 projecting from the base 50*r*. The raised portion 62 defines a convoluted cam channel 64. Located between the convoluted cam channel 64 and the slot 48, defined by the bottom wall 54, is a circular boss 66 which surrounds an extending rod 68. The post 68, as explained below, acts as a pivot point for the pivot arm 40 containing the blade 42.

Referring to FIGS. 3 and 3B, the rear housing 24 has a second circular boss 70 defining an indentation 72 for receiving a portion of the spring post 34. The indentation 72 has a bi-level surface 74 at the base 50*r*; the bi-level surface includes a raised level 76 on either side of a lower groove 78. In the center of the lower groove 78 is the hole 32 seen in FIG. 1.

Still referring to FIG. 3, the rear housing section 24 has a post 80 that projects upward. The post 80 engages the base 50*f* of the front housing section 26 as described below. The base 50*r*, in addition, forms a ridge 82 upon which the trigger mechanism 28 slides. The top wall 58*r* of the housing section 24 has a projecting member 84, a stop member, which projects into the inner space 46 for limiting movement of the trigger mechanism 28.

Figure 4A:
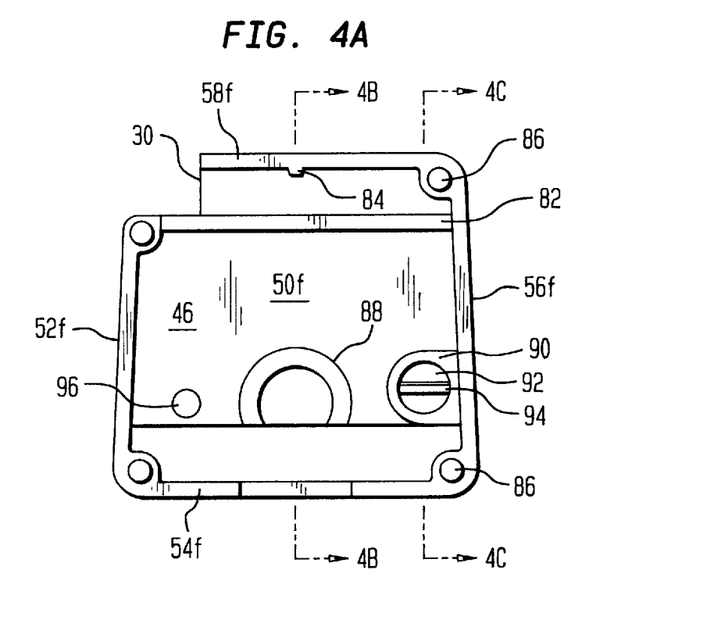
FIG. 4A is a sectional view taken along the line 4A—4A in FIG. 4.
Figures 4B, 4C:
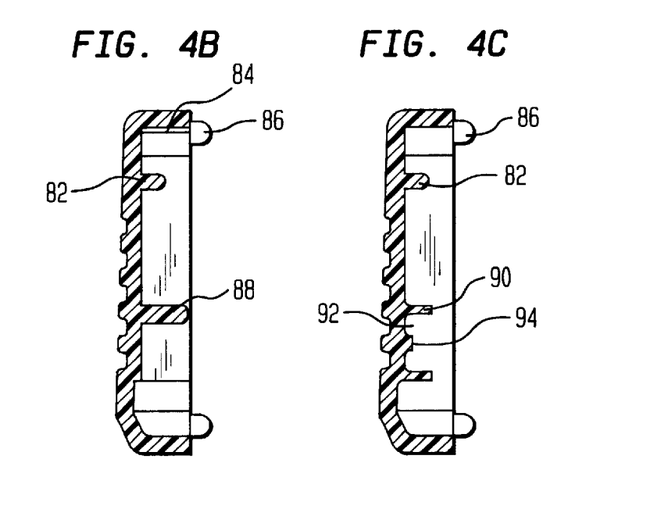
FIG. 4B is a sectional view taken along the line 4B—4B in FIG. 4.

The base 50*f* and the four walls 52*f*, 54*f*, 56*f*, and 58*f* projecting from the base 50*r* of the front housing sections 26 are seen in FIG. 4. The four walls 52*f*, 54*f*, 56*f*, and 58*f* and base 50*f* define a portion of the inner space 46. Located generally in the locations where two walls join to form a corner are pins 86, as seen in FIGS. 4, 4A, and 4B, which are received by the openings 60 in the rear housing section 24.

Referring to FIGS. 4 and 4A, the front housing section 26 has a semi-circular boss 88 for holding the pivot arm 40 containing the blade 50 in position, as explained below.

The top wall 58*f* of the housing section 26 has a projecting member 84, a stop member, which projects into the inner space 46 for limiting movement of the trigger mechanism 28. The front housing section 26 has a circular boss 90 defining an indentation 92 for receiving a portion of the spring post 34 as seen in FIGS. 4 and 4B. The indentation 92 has a raised protrusion 94 at the base 50*f*.

Still referring to FIG. 4, the front housing section 26 has a dimple 96 for receiving the tip of the post 80 that projects from the rear housing section 24. The base 50*f*, in addition, forms a ridge 82 upon which the trigger mechanism 28 slides.

Figure 5A:
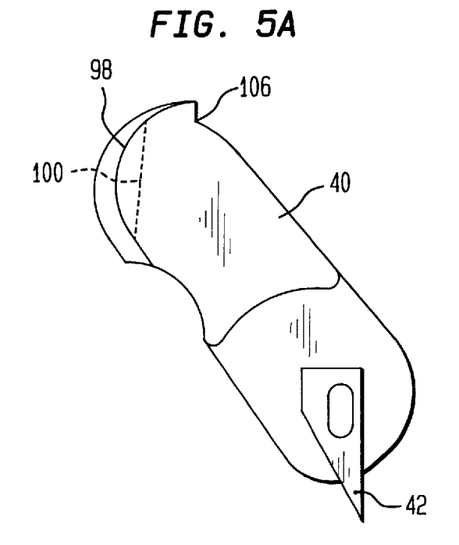
FIG. 5A is a front view of a pivot arm and a cutting edge employed in this invention.

Referring to FIG. 5A, the pivot arm 40 has a shoulder 98 defined by two different level surfaces. The shoulder 98 is engaged by the torsion spring 44, as defined below. A recess 100 is formed for part of the shoulder 98, and is shown in hidden line. The blade 42, a triangular blade with a cutting edge 102 and a sharpened apex 104 is coupled to the pivot arm 40. The blade 42 may be secured to the pivot arm 40 by any conventional means and is scalpel-like in appearance and function. Located on the top of the pivot arm 40 is a keeper section 106 which acts with the end of the trigger mechanism 28 to retain the pivot arm 40 in a first position prior to actuation of the skin incision apparatus 20.

Figure 5B:
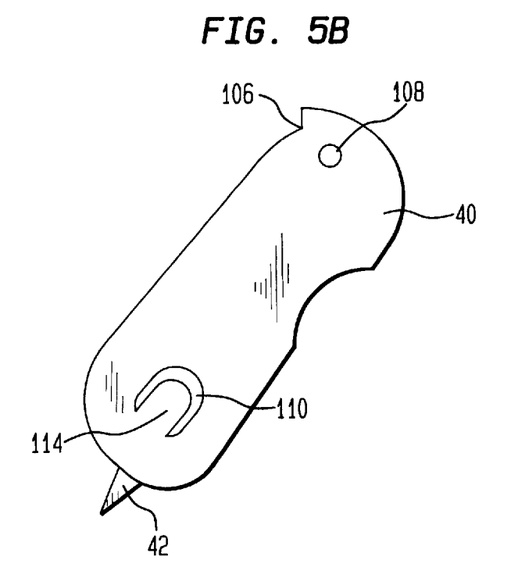
FIG. 5B is a rear view of the pivot arm and the cutting edge.

Referring to FIG. 5B, the pivot arm 40 has an extended cam follower rod 108 which extends into the convoluted cam channel 64. The convoluted cam surface of the cam channel 64 controls the movement of the pivot arm 40 and, therefore, of the cutting edge 102 of the blade 42 when the skin incision apparatus 20 is activated. A raised boss 110 projects from the pivot arm 40 to define an elongated aperture 114.

Figure 6A:
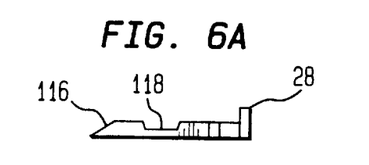
FIG. 6A is a front view of a trigger mechanism or plunger employed in this invention.
Figure 6B:
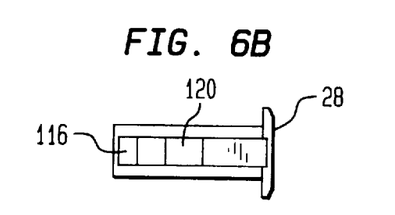
FIG. 6B is a bottom view of the trigger mechanism.

The trigger mechanism 28 has a sloping front end 116 as seen in FIG. 6A which acts with the keeper section 106 of the pivot arm 40 during operation. The trigger mechanism 28 also contains a top channel 118 which abuts against the stop member 84 of the housing 22. Referring to FIG. 6B, the trigger mechanism 28, also referred to as a plunger member, has a hollow section 120 through which the keeper section 106 of the pivot arm 40 passes as it moves, as explained below.

Figure 7:
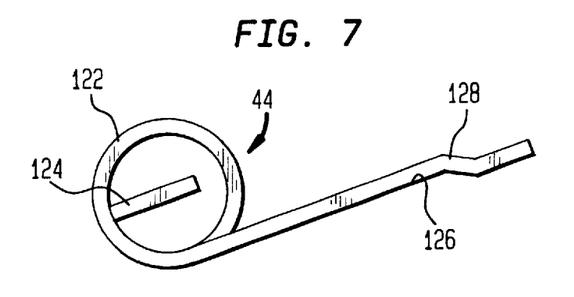
FIG. 7 is an enlarged front view of a torsion spring.

FIG. 7 is an enlarged side view of the torsion spring 44. The spring 44 has a core 122 and a pair of legs 124 and 126. The first leg 124 projects inwardly and bisects the core 122. The second leg 126 extends generally out at a tangent from the core 122. The second leg 126 has a bend or jog 128, which facilitates assembly as discussed below.

Figure 8A:
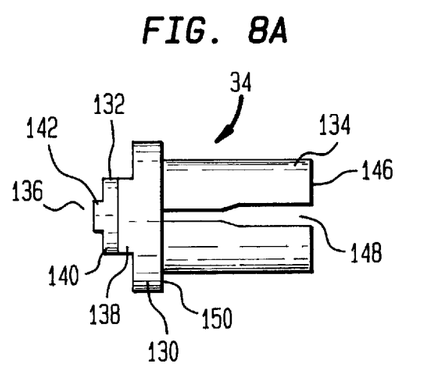
FIG. 8A is a side view of a spring post.
Figure 8B:
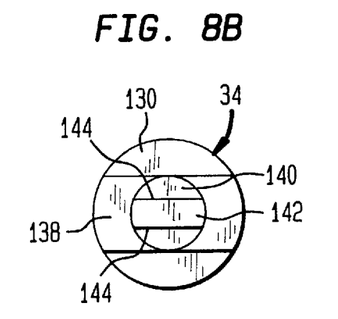
FIG. 8B is a front view of the spring post.
Figure 8C:
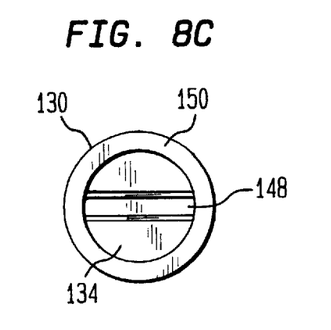
FIG. 8C is a rear view of the spring post.

Referring to FIGS. 8A, 8B, and 8C, the spring post 34 is adapted to carry the spring 44. The spring post 34 generally has a cylindrical shape and includes a cylindrical base portion 130, a raised detent portion 132, and a reduced diameter cylindrical portion 134. The raised detent portion 132 projects from the cylindrical base portion 130 to a first end 136. The raised detent portion 132 has a circular segment detent portion 138 projecting from the cylindrical base portion 130. A cylindrical guide portion 140 projects from the detent portion 138. The cylindrical guide portion 140 has an outside diameter no greater than the width of the circular segment detent portion 138 and is received by the hole 32 in the rear housing section 24, as seen in FIGS. 1 and 3. A turn element 142 for setting or loading the spring 34, as described below, projects from the end of the cylindrical guide portion 140. The turn element 142, similar to the circular segment detent portion 138, has a pair of parallel edges 144 spaced by circular arc edges, in a preferred embodiment, as best seen in FIG. 8B.

The reduced diameter cylindrical portion 134 of the spring post 34 extends from the base portion 130 to a second end 146. A slot 148 in the reduced diameter cylindrical portion 134 extends from the second end 146 to approximately the cylindrical base portion 130. The intersection of the base portion 130 with the reduced diameter cylindrical portion 134 defines a shoulder 150.

Figure 9A:
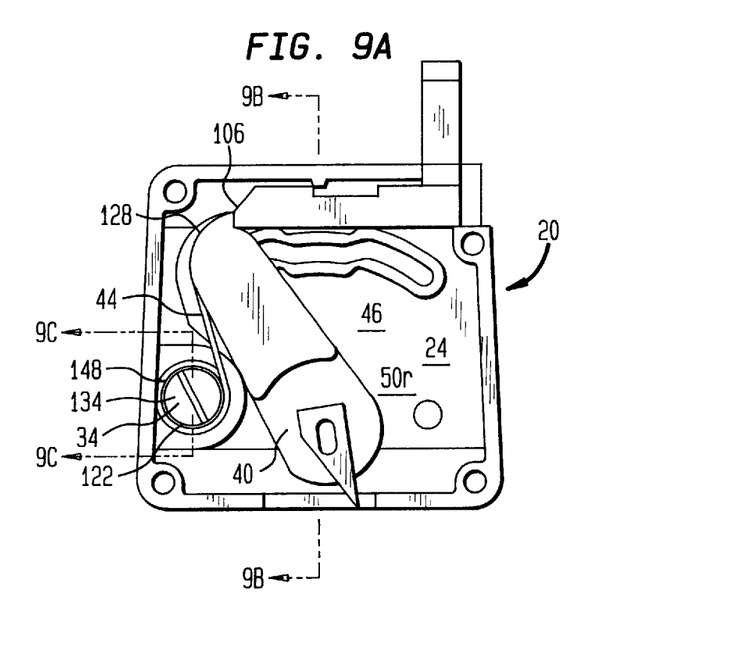
FIG. 9A is a sectional view taken along the line 9A—9A in FIG. 9.
Figure 9B:
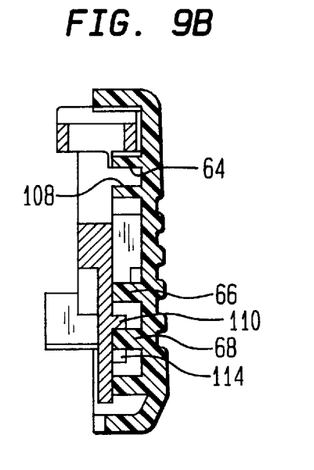
FIG. 9B is a sectional view taken along the line 9B—9B in FIG. 9.
Figure 9C:
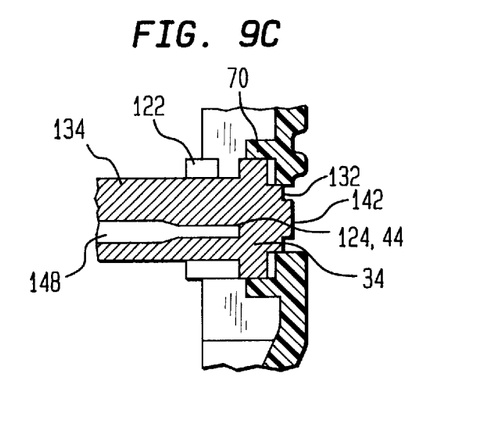
FIG. 9 is an inside view of a first housing section with the pivot arm, and the spring and the spring post installed in an installation position.

Referring to FIGS. 9 and 9A, the skin incision apparatus 20 is assembled by placing the pivot arm 40 in the rear housing section 24 such that the extended cam follower rod 108 is received by the convoluted cam channel 64 and the elongated aperture 114 defined by the raised boss 110, as best seen in FIGS. 9A and 5B, receives the extending rod 68 of the rear housing section 24. The pivot arm 40 is positioned in the first position, the actuation position, with the keeper section 106 to the left in FIG. 9.

Prior to installing the torsion spring 44 and the spring post 34, the leg 124 is received by the slot 148 in the reduced diameter cylindrical portion 134 of the spring post 34, such that the core 122 of the spring 44 encircles the reduced diameter portion 134 of the post 34. The spring 44 is located on the shoulder 150 defined by the base portion 130 and the reduced diameter cylindrical portion 134. Referring to FIGS. 9 and 9B, the spring post 34 is positioned on the rear housing section 24 so that the raised detent portion 132 of the spring post 34 is received by the second circular boss 70 on the base 50 of the rear housing section 24. The circular segment detent portion 138 is positioned so that it does not align with the lower groove 78 of the bi-level surface 74, as best seen in FIG. 9B. The turn element 142, in a preferred embodiment, is located in the hole 32 in the base 50 of the rear housing section 26. The second leg 128 is received by the shoulder 98 in the pivot arm 40. The bend or jog 128 in the leg 126 of the spring 44 reduces the chance of interference with the front housing section 26 during assembly.

The trigger mechanism 28 is installed on the ridge 82. The sloping front end 116 is positioned to engage the keeper section 106 of the pivot arm 40. The top channel 118 is positioned to receive the stop member 84. The keeper or safety device 38 can be installed on the trigger mechanism 28 at this time.

Figure 10A:
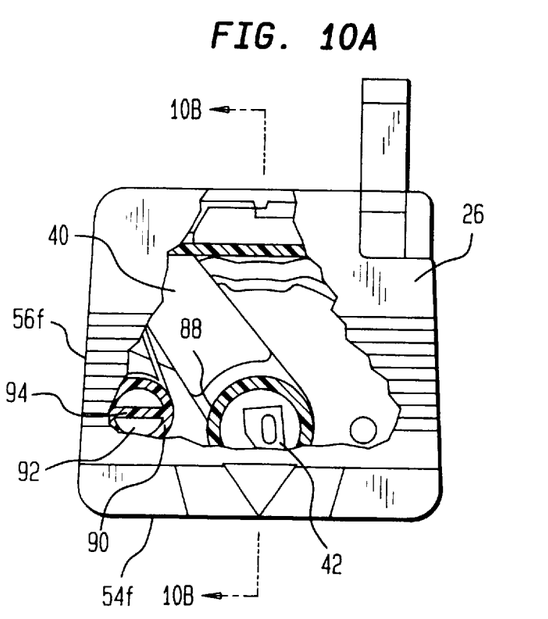
FIG. 10A is a sectional view taken along the line 10A—10A in FIG. 10.
Figure 10B:
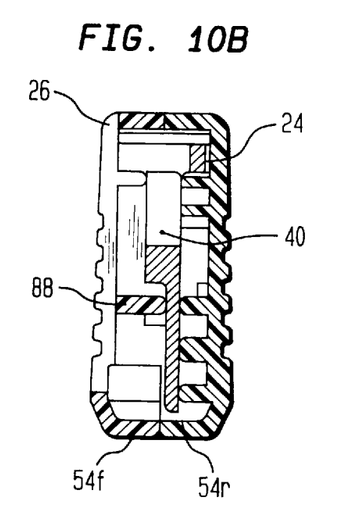
FIG. 10 is a front view of the apparatus with a portion of the base of the front housing section broken away to show the interior.

Referring to FIGS. 10 and 10A, the front housing section 26, is positioned on top of the rear housing section 24 such that the pins 86, as seen in FIG. 4, are received by the openings 60, as seen in FIG. 9, in the rear housing section 24. The semi-circular boss 88 of the front housing section 26 is positioned above the pivot arm 40, in proximity to where the blade 42 is mounted to the pivot arm 40. The reduced diameter cylindrical portion 134 of the spring post 34 is received in the indentation 92 defined by the circular boss 90 of the front housing section 26. The slot 148 is not aligned with the raised protrusion 94 in the circular boss 90, at least initially. The position of the slot 148 is shown in FIG. 9.

With the circular segment detent portion 138 of the spring post 34 not located in the lower groove 78 of the bi-level surface 74 of the second circular boss 70 of the rear housing section 24 and the raised protrusion 94 on the front housing section 26 not received by the slot 148 of the spring post 34, the walls 52, 54, 56, and 58 of the two housing sections 24 and 26 do not engage completely, specifically walls 54 and 56 which are close to the spring post 34.

Figure 11:
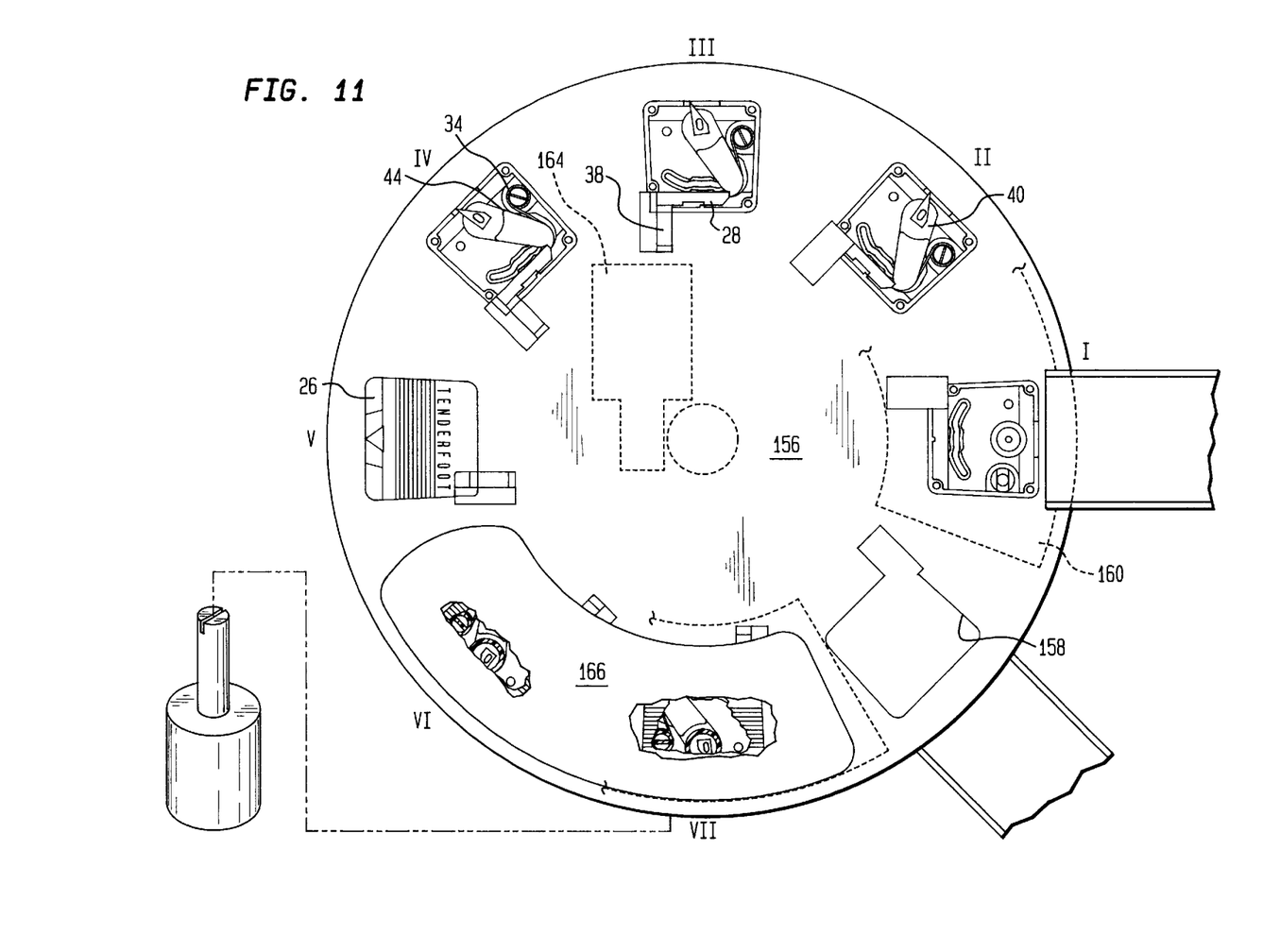
FIG. 11 is a top view of a turntable for automatically assembly with various components shown broken away or in hidden line.

With the two housing sections 24 and 26 held together, the turn element 142 is rotated using a tool 154, as seen in FIG. 11, which complements the shape of the turn element. The turn element 142 is turned clockwise as seen in FIGS. 9 and 10, and counterclockwise as seen in FIG. 1. The rotation of the turn element 142 rotates the spring post 34, therein moving the first leg 124 of the spring 44 which is received by the slot 148 in the reduced diameter cylindrical portion 134 of the spring post 34. In the assembly, the first leg 124 is the movable end or leg to tension the spring 44. The second leg 126, which is received by the shoulder 98 of the pivot arm 40, is the stationary end. The turn element 142 is rotated until the circular segment detent portion 138 of the spring post 34 aligns with the lower groove 78 of the bi-level surface 74 of the second circular boss 70 of the rear housing section 24 and the raised protrusion 94 on the front housing section 26 is received by the slot 148 of the spring post 34. With the alignment, the walls 52, 54, 56, and 58 of the two housing sections 24 and 26 do mesh, as shown in FIG. 10A.

With the spring 44 wound and the housing 22 closed, the skin incision apparatus 20 is ready to operate. The keeper 38 is removed from the trigger mechanism 28. The trigger mechanism 28 is pushed inward, to the left in FIG. 1A. As the trigger mechanism 28 is pushed, the sloping front end 116 pushes the pivot arm 40 towards the left until the pivot arm 40 clears the sloping front end 116 of the trigger mechanism 28. With the pivot arm 40 cleared, the spring 44 pivots the entire pivot arm 40. As the spring rotates the pivot arm 40, the second leg 126 rotates and is the movable end, and the first leg 124, the stationary end, is held by the spring post 34 which is held by the bi-level surface 74 of the rear housing section 24 and the raised protrusion 94 of the front housing section 26.

The pivot arm 40 moves with the extended cam follower rod 108 following the convoluted cam channel 64. The shape of the convoluted cam channel 64 converts the generally arcuate motion of the pivot arm 40 into a linear portion for a segment of the motion of the blade 42. The operation is such that the apex 104 of the blade 42 punctures the skin and thereafter the cutting edge 102 incises the skin. At the end of travel, the blade 42, including the apex 104, is withdrawn from the skin back into the housing 22.

It is recognized that assembly could occur without assistance of humans, such as on a turntable 156 as shown in FIG. 11. The turntable 156 has a plurality of orifices 158 which are of a shape similar to that of the rear housing section 24, with an additional notch for the placing of the keeper 38. In a preferred embodiment, the turntable 156 has eight (8) orifices 158. The turntable 158 has a plate 160, shown in hidden line, which is generally annular and underlies all of the orifices 158, except one as explained below, for retaining the skin incision apparatus 20.

The rear housing section 24 slides into an orifice 158 from a ramp 162 at station I. The turntable is rotated, by a motor mechanism 164 shown in hidden line, to the next position, or station. While the next rear housing section 24 is being loaded into the next orifice 158, the pivot arm 40 is loaded by a robotic arm, not shown, at the next station (station II) into the rear housing section 24. In the next station (station III), after rotation of the turntable 156, the trigger mechanism 28 and keeper 38 are loaded as a unit. The keeper 38 is loaded on the trigger mechanism 28 prior to installation in station III.

Prior to installing the torsion spring 44 and the spring post 34, the leg 124 of the spring 44 is received by the slot 148 in the reduced diameter cylindrical portion 134 of the spring post 34, such that the core 122 of the spring 44 encircles the reduced diameter portion 134 of the post 34. The spring 44 is located on the shoulder 150 defined by the base portion 130 and the reduced diameter cylindrical portion 134. The spring post 34 is positioned on the rear housing section 24 (in station IV) so that the raised detent portion 132 of the spring post 34 is received by the second circular boss 70 on the base 50 of the rear housing section 26, similar to that described above with reference FIGS. 9 and 9B. The second leg 128 is received by the shoulder 98 of the pivot arm 40.

With all the parts located on the rear housing section 24, the front housing section 26 is positioned on the rear housing section 24 in station V. The pins 86, as seen in FIG. 4, of the front housing section 26 are received by the openings 60 in the rear housing section 24. As indicated above, the walls 52, 54, 56, and 58 of the two housing sections 24 and 26 do not engage completely. The turntable rotates moving the housing sections 24 and 26 under a spring loaded plate 166, which urges the front housing section 26 into engagement with the rear housing section 24. The spring loaded plate 166 overlies stations VI and VII. In a preferred embodiment, no operation occurs at station VI.

At the next station (Station VII), a tool 154, shown exploded away in FIG. 11, moves into engagement with the turn element 142 of the spring post 34, as seen in FIGS. 1 and 9B, rotates the spring post 34, therein moving the first leg 124 of the spring 44 which is received by the slot 148 in the reduced diameter cylindrical portion 134 of the spring post 34. The turn element 142 is rotated until the circular segment detent portion 138 of the spring post 34 aligns with the lower groove 78 of the bi-level surface 74. The spring loaded plate 166 urges the front housing section into engagement with the rear housing section.

The turntable 156 rotates to a final station (station VIII) where the underlying plate 160 is not located. The skin incision apparatus 20 drops to a chute 168 or a conveyor, to move to a packaging section, not shown. It is recognized that the turntable 156 could have fewer or more stations. It is also recognized that multiple parts could be loaded at one station or a plurality of stations could have the same operation being performed and the turntable turns a plurality of orifices at one time. In addition, it is recognized that there are other methods of assembling the skin incision apparatus 20 automatically.

The present invention may be embodied in other specific forms without departing from the spirit or essential attributes therefore and, accordingly, references should be made to appended claims, rather than to the foregoing specification, as indicating the scope of the invention.

We claim:

1. A method of assembling a skin incision apparatus, comprising the following steps:
   providing a housing having at least first and second housing sections, each housing section having a base, the first housing section having a cam and a pivot point carried by the base;
   installing a moveable arm having a pin and an opening on the first housing section with the pin of the moveable arm received by the cam on the base and the opening receiving the pivot point of the housing;
   installing a spring bias means on a spring carrying means;
   installing the spring carrying means on the first housing section;
   installing the second housing section over the first housing section such that the moveable arm, the spring bias means, and the spring carrying means are interposed between the bases of the housing sections, wherein a portion of the spring carrying means contained within the housing is externally accessible; and
   rotating the portion of the spring carrying means which is externally accessible to move the spring bias means from an installation position to a loaded position after the second housing section has been installed over the first housing section.

2. A method of assemblying a skin incision apparatus as in claim 1, comprising the following step of installing a trigger mechanism adapted for engaging the movable arm, on the base of the first housing prior to installing the second housing section.

3. A method of assembling a skin incision apparatus as in claim 1 wherein the step of installing the spring carrying means on the first housing section further comprises positioning a leg of the spring bias means on a shoulder on the movable arm.

4. A method of assembling a skin incision apparatus as in claim 1 wherein the portion of the spring carrying means which is externally accessible comprises a turn element, the step of rotating the spring carrying means further comprising the step of engaging a tool against the turn element of the spring carrying means and rotating the tool.

5. A method of assembling a skin incision apparatus as in claim 4 wherein the step of rotating the spring carrying means further comprises rotating the spring carrying means such that a circular segment detent portion of the spring carrying means is retained in a lower groove of an indentation in the base of one of the first and second housing section.

6. A method of assemblying a skin incision apparatus, comprising the following steps:
   providing a turntable having a plurality of orifices, each orifice adapted to receive a skin incision housing section;
   placing a housing section having a base and a plurality of walls into an orifice on the turntable, the housing section defining an inner space which opens upward, the housing section having a cam and a pivot point integral with the base;
   installing a pivot arm in the housing section;
   installing a trigger mechanism in the inner space of the housing section, the trigger mechanism adapted to engage a keeper section on the pivot arm;
   installing a spring post carrying a torsion spring in the housing section such that a turn element of the spring post extends through an opening in the base of the housing;
   installing a second housing section having a base, over the first housing section such that the pivot arm, the spring post, and the spring are interposed between the bases of the housing sections; and
   rotating the spring post to move the spring from an installation position to a loaded position.

7. A method of assemblying a skin incision apparatus as in claim 6, comprising the following additional steps:

installing a keeper on the trigger mechanism prior to installing the trigger mechanism in the inner space of the housing; and installing the torsion spring on the spring post prior to installing the spring post in the inner space of the housing section.

8. A method of assembling a skin incision apparatus as in claim 6 wherein the step of installing the spring carrying means on the first housing section further comprises positioning a leg of the spring on a shoulder on the pivot arm.

* * * * *